(12) United States Patent
Jones et al.

(10) Patent No.: US 6,350,884 B1
(45) Date of Patent: Feb. 26, 2002

(54) ACRYLIC AND PROPIONIC ACID COMPOUNDS, INTERMEDIATES, PROCESSES, COMPOSITIONS, AND METHOD

(75) Inventors: Charles David Jones, Indianapolis; Alan David Palkowitz, Carmel; Kenneth Jeff Thrasher, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/940,785

(22) Filed: Sep. 30, 1997

Related U.S. Application Data

(62) Division of application No. 08/673,702, filed on Jun. 25, 1996.

(51) Int. Cl.$^7$ .............................................. C07D 333/60
(52) U.S. Cl. ........................ 549/57; 540/609; 540/610; 544/165; 546/202; 548/525
(58) Field of Search .............................. 514/212, 237.8, 514/238.2, 319, 324, 422, 443, 448; 540/609, 610; 544/165; 546/202; 548/525; 549/57

(56) References Cited

U.S. PATENT DOCUMENTS

| | | | | |
|---|---|---|---|---|
| 3,274,213 A | 9/1966 | Lednicer | ..................... | 546/205 |
| 3,293,263 A | 12/1966 | Lednicer | ..................... | 546/205 |
| 3,313,853 A | 4/1967 | Lednicer | ..................... | 546/205 |
| 3,320,271 A | 5/1967 | Lednicer | ..................... | 548/570 |
| 3,394,125 A | 7/1968 | Crenshaw | ..................... | 548/525 |
| 3,396,169 A | 8/1968 | Lednicer | ..................... | 546/205 |
| 3,413,305 A | 11/1968 | Crenshaw | ..................... | 548/525 |
| 3,483,293 A | 12/1969 | Duncan et al. | ............. | 546/205 |
| 3,567,737 A | 3/1971 | Lednicer | ..................... | 546/205 |
| 3,862,232 A | 1/1975 | Lednicer | ..................... | 564/324 |
| 4,133,814 A | 1/1979 | Jones et al. | ................. | 546/202 |
| 4,230,862 A | 10/1980 | Suarez et al. | ............... | 546/237 |
| 4,380,635 A | 4/1983 | Peters | ........................ | 546/202 |
| 4,418,068 A | 11/1983 | Jones | ........................ | 514/320 |
| 5,254,568 A | 10/1993 | Kapil et al. | ................. | 514/320 |
| 5,827,876 A | * 10/1998 | Sabatucci | ................... | 514/448 |

FOREIGN PATENT DOCUMENTS

| | | |
|---|---|---|
| EP | 0 124 369 | 11/1984 |
| WO | WO93/10113 | 5/1993 |
| WO | WO93/1074 | 6/1993 |
| WO | WO95/10513 | 4/1995 |

OTHER PUBLICATIONS

Crenshaw, R.R., et al., *J. Med. Chem.*, 14(12):1185–1190 (1971).
Durani, N., et al., *Indian J. Chem.*, 22B:489–490 (1983).
Jones, C.D., et al., *J. Med. Chem.*, 35:931–938 (1992).
Cerny, et al., *Tetrahedran Letters*, 8:691–694 (1972).
Lednicer, D., et al., *J. Med. Chem.*, 8:52–57 (1964).
Lednicer, D., et al., *J. Med. Chem.*, 9:172–175 (1965).

* cited by examiner

*Primary Examiner*—Ceila Chang
(74) *Attorney, Agent, or Firm*—Gary M. Birch

(57) ABSTRACT

This invention is directed to a class of acrylic and propionic acid compounds and their use in the treatment of post-menopausal symptoms and restenosis. In other embodiments, the invention is directed to intermediates and to processes for the preparation of the acrylic and propionic acid compounds.

6 Claims, No Drawings

ACRYLIC AND PROPIONIC ACID COMPOUNDS, INTERMEDIATES, PROCESSES, COMPOSITIONS, AND METHOD

This application is a division of application Ser. No. 08/673,702 filed Jun. 25, 1996.

FIELD OF THE INVENTION

This invention relates to the fields of pharmaceutical and organic chemistry and provides novel acrylic and propionic acid compounds which are useful for the treatment of various medical indications associated with post-menopausal syndrome. The present invention further relates to intermediate compounds and processes useful for preparing the pharmaceutically active compounds. The invention also provides novel methods of treatment and compositions useful in carrying out the methods.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, two major effects of post-menopausal syndrome are the source of great long-term medical concern: osteoporosis and cardiovascular effects such as hyperlipidemia.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

In response to the clear need for new pharmaceutical agents which are capable of alleviating the symptoms of post-menopausal syndrome, the present invention provides new acrylic and propionic acid compounds, pharmaceutical compositions thereof, and methods of using such compounds for the treatment of osteoporosis and the cardiovascular effects of post-menopausal syndrome.

The present invention also provides these same acrylic and propionic acid compounds for the treatment of restenosis.

Smooth aortal muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase occurring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal*, 122: 171–187 (July 1991).

In the pathogenesis of restenosis, excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

SUMMARY OF THE INVENTION

The present invention relates to compounds of Formula I:

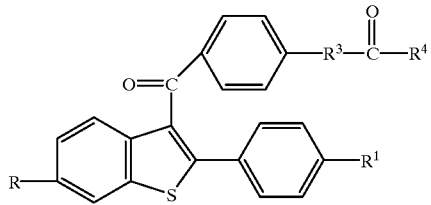

wherein
each of R and $R^1$ is independently hydrogen, hydroxy, $C_1$–$C_4$-alkoxy, benzyloxy, $C_1$–$C_6$-alkanoyloxy, benzyloxy, substituted benzyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$-alkylsulfonyloxy;
$R^3$ is —CH=CH— (trans) or —$CH_2$—$CH_2$—;
$R^4$ is hydroxy, $C_1$–$C_4$-alkoxy, or —N($R^5$)$_2$ wherein each $R^5$ is taken separately and independently represents hydrogen or $C_1$–$C_6$-alkyl, or both $R^5$ are taken with the N atom and constitute pyrrolidino, piperidino, hexamethyleneimino, or morpholino; or a pharmaceutically acceptable salt thereof.
Preferred compounds are those wherein
$R^3$=—CH=CH— (trans);
$R^4$=—OH (including salts) or —OEt ; or
R and $R^1$=OH or $OCH_3$.
Compounds embodying multiple preferences, in any combination, are also preferred.

Also provided by the present invention are intermediate compounds of Formula Ia, which are useful for preparing the pharmaceutically active compounds of the present invention, and which are shown below

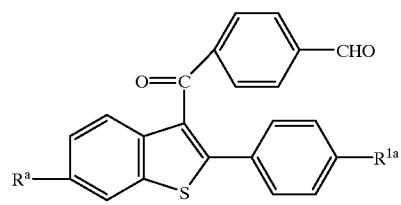

wherein each of $R^a$ and $R^{1a}$ is independently hydrogen, $C_1$–$C_4$-alkoxy, benzyloxy, $C_2$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_{1-5}$-alkoxycarbonyloxy, or $C_4$–$C_6$-alkylsulfonyloxy.

The present invention further relates to pharmaceutical compositions containing compounds of Formula I, optionally containing estrogen or progestin, and the use of such compounds, alone, or in combination with estrogen or progestin, for alleviating the symptoms of post-menopausal syndrome, particularly osteoporosis and cardiovascular related pathological conditions.

The compounds of the present invention also are expected to be useful in inhibiting aortal smooth muscle cell proliferation, particularly restenosis, in humans.

DETAILED DESCRIPTION OF THE INVENTION

Most of the compounds of Formula I are made by conversion of the formylbenzoyl compounds of Formula Ia:

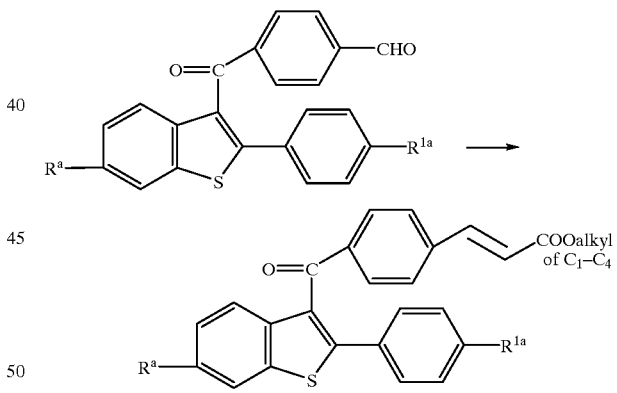

This conversion is an example of a Horner-Emmons reaction, which is discussed in detail by Wadsworth in *Organic Reactions*, 1977, 25, 73–253, which is incorporated herein by reference.

The conversion of the p-formylbenzoyl compounds is achieved by reacting a compound of Formula Ia with the carbanion of a trialkyl phosphonoacetate. This carbanion is generated by pretreating the trialkyl phosphonoacetate with a strong base, such as n-butyllithium, sodium hydride, and DBU. The reaction is conducted in an inert solvent; suitable such solvents include tetrahydrofuran, dioxane, benzene, 1,2-dimethoxyethane, and diethyl ether. The reaction is conducted at temperatures of from −78° to 0°. The amounts of the reactants are not critical; the reaction consumes equimolar amounts of the p-formylbenzoyl compound and the trialkyl phosphonoacetate carbanion. The product is isolated from the reaction mixture in conventional manner.

In Formula Ia, Ra and $R^{1a}$ represent any of the groups defined for R and $R^1$ exclusive of hydroxy. This reaction is conducted with any hydroxy group having first been protected. Hydroxy protection is well known; see, for example, *Protective Groups in Organic Chemistry*, Plenum Press (London and New York, 1973); *Protecting Groups in Organic Synthesis*, Wiley (New York, 1981); and *The Peptides*, Vol. I, Schrooder and Lubke, Academic Press (London and New York, 1965). Hydroxyl protection is also discussed in U.S. Pat. No. 4,418,068, which is incorporated herein by reference. The following R and $R^1$ groups are in the nature of hydroxy protecting groups: $C_1$–$C_4$-alkoxy, benzyloxy, $C_1$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, and $C_4$–$C_6$-alkylsulfonyloxy. These compounds are primarily useful as chemical intermediates, but some of them exhibit useful biological activity in addition.

Other compounds of the present invention are prepared in standard manners well known to those skilled in the art. The free acids ($R^4$=OH) are prepared by hydrolysis; the resulting acids can be reacted subsequently with alkanols to form other esters, or with amines to form the amides. Deprotection of the hydroxy protecting groups is done by well known procedures, which are discussed in the reference cited above. Hydrogenation of the $R^3$=—CH=CH— compounds yields the corresponding $R^3$=—CH$_2$—CH$_2$— compounds.

Therefore, in one embodiment the present invention is directed to a method of preparing a compound of Formula Ib.

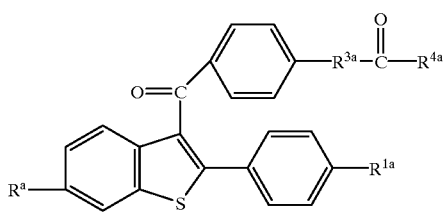

Ib wherein each of $R^a$ and $R^{1a}$ is independently hydrogen, $C_1$–$C_4$-alkoxy, benzyloxy, $C_2$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_{1-5}$-alkoxycarbonyloxy, or $C_4$–$C_6$-alkylsulfonyloxy;

$R^{3a}$ is —CH=CH— (trans); and $R^{4a}$ is $C_1$–$C_4$-alkoxy, which comprises reacting a compound of Formula Ia

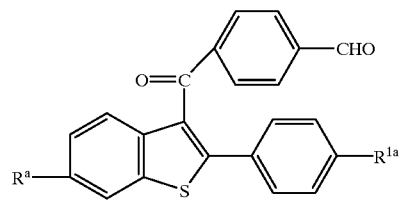

Ia with a trialkyl phosphonoacetate carbanion in an inert solvent at a temperature from −78° to 0°. Optionally, any one or more additional reactions are thereafter conducted:

hydrolyzing the ester to an acid, removing hydroxy protecting groups, hydrogenating CH=CH to CH$_2$—CH$_2$, and converting the acid to an ester, amide, or salt.

The present compounds can be used for the purposes described herein in the free-acid form ($R^4$=hydroxy). However, it is feasible and sometimes preferred to use pharmaceutically acceptable salts, such as an ammonium salt; or an inorganic alkali metal salt, e.g., sodium or potassium, or an organic amine salt such as methylamine, diethylamine, triethylamine, pyridine, morpholine, n-butylamine, and octadecylamine. The preparation of such salts is well known. Typically the compound of Formula I is reacted with an equimolar or excess amount of base. The reactants are generally combined in a mutual inert solvent; the salt normally precipitates out of solution and can be isolated by filtration, or the solvent can be removed by conventional means.

The p-formylbenzoyl compounds, Formula Ia, represent another embodiment of the present invention. They are prepared by the following reaction scheme:

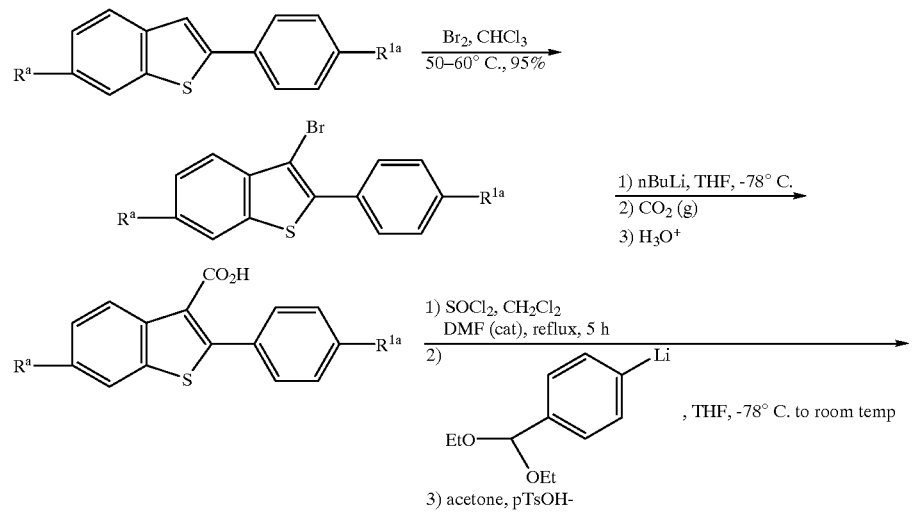

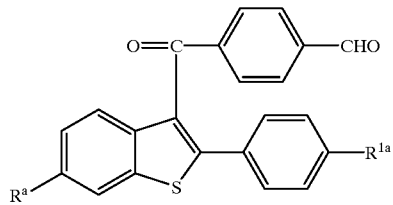

which is more fully illustrated by Preparations 1–3, below. The benzo[b]thiophenes which are employed as starting materials are prepared as described in U.S. Pat. Nos. 4,418,068 and 4,133,814, which are incorporated herein by reference. The latter of these also describes the preparation of the 1-carboxy-2-phenylbenzo[b]thiophenes, by another route than above.

Preparation 1

6-methoxy-2-(4-methoxyphenyl)-3-bromobenzo[b]thiophene

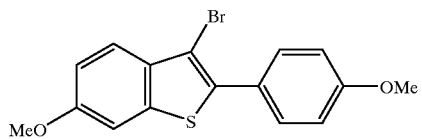

To a solution of 6-methoxy-2-(4-methoxyphenyl)benzo[b]thiophene (27.0 g, 100 mmol) in 1.10 L of $CHCl_3$ at 60° C. was added bromine (15.98 g, 100 mmol) dropwise as a solution in 200 mL of $CHCl_3$. After the addition was complete, the reaction was cooled to room temperature, and the solvent removed in vacuo to provide 34.2 g (100%) of 6-methoxy-2-(4-methoxyphenyl)-3-bromobenzo[b]thiophene as a white solid. mp 83–85° C. $^1$H NMR (DMSO-$d_6$) δ7.70–7.62 (m, 4H), 7.17 (dd, J=8.6, 2.0 Hz, 1H), 7.09 (d, J=8.4 Hz, 2H). FD mass spec: 349, 350. Anal. Calcd. for $C_{16}H_{13}O_2SBr$: C, 55.03; H, 3.75. Found: C, 54.79; H, 3.76.

Preparation 2

Preparation of 6-methoxy-2-(4-methoxyphenyl)-3-carboxybenzo[b]thiophene

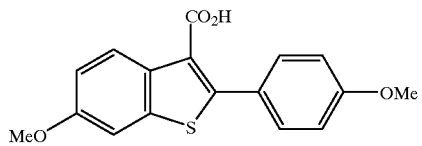

6-Methoxy-2-(4-methoxyphenyl)-3-bromobenzo[b]thiophene (15.0 g, 42.9 mmol) was dissolved in 300 mL of anhydrous THF under $N_2$ and cooled to −70° C. To this solution was added nBuLi (29.6 mL, 47.4 mmol, 1.6 M solution in hexanes) dropwise via syringe. After stirring at −70° C. for 20 min, a steady stream of $CO_2$ (g) was introduced into the reaction mixture for 15 min. The mixture was allowed to gradually warm to 0° C. and then quenched by pouring the mixture into cold 1 N HCl (500 mL). The aqueous layer was extracted with EtOAc (3×300 mL). The organic layer was dried ($Na_2SO_4$) and concentrated in vacuo to a solid. The crude product was chromatographed ($SiO_2$, 25% EtOAc/hexanes) to provide 9.35 g (69%) of 6-methoxy-2-(4-methoxyphenyl)-3-carboxybenzo[b]thiophene as a white solid. mp 166–170° C. $^1$H NMR (DMSO-$d_6$) δ (doubling due to rotamers) 13.0–12.8 (bs), 8.10 and 7.68 (d, J=8.1 Hz, 1H), 7.63 and 7.47 (d, J=8.6 Hz, 2H), 7.59 and 7.54 (d, J=2.0 Hz, 1H), 7.10 and 6.97 (dd, J=8.1, 2.0 Hz, 1H), 7.02 (d, J=8.6 Hz, 2H), 3.83 and 3.79 (s, 3H), 3.82 and 3.80 (s, 3H). FD mass spec: 315. Anal. Calcd. for $C_{17}H_{14}O_4S$: C, 64.95; H, 4.49. Found: C, 65.19; H, 4.32.

Preparation 3

6-methoxy-3-(4-formylbenzoyl)-2-(4-methoxyphenyl)benzo[b]thiophene.

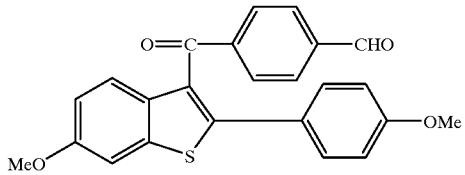

To a solution of 6-methoxy-2-(4-methoxyphenyl)-3-carboxybenzo[b]thiophene (4.00 g, 12.74 mmol) in 100 mL of anhydrous $CH_2Cl_2$ was added thionyl chloride (3.0 mL, 38.22 mmol) along with 0.1 mL of DMF. The resulting mixture was heated to reflux for 5 h. Upon cooling, the solvent and excess thionyl chloride were removed in vacuo to give the acid chloride as a yellow oil. The acid chloride was then dissolved in 75 mL of THF under $N_2$.

In a separate flask, 4-bromobenzaldehyde diethyl acetal (3.65 g, 14.0 mmol) was dissolved in 50 mL of anhydrous THF under $N_2$ and cooled to −78° C. To this solution was added nBuLi (8.,76 mL, 14.0 mmol, 1.6 M solution in hexanes) dropwise via syringe. After stirring for 20 min at −78° C., the solution was transferred via cannula to a −78° C. solution of the acid chloride. The resulting mixture was allowed to gradually warm to room temperature, and then quenched by pouring into cold 0.2 N NaOH (200 mL). The aqueous was extracted with EtOAc (2×200 mL). The organic layer was dried ($Na_2SO_4$) and concentrated in vacuo to give crude 6-methoxy-3-[(4-diethoxymethyl)benzoyl]-2-(4-methoxyphenyl)benzo[b]thiophene as a yellow oil. This material was immediately dissolved in 200 mL of reagent grade acetone, and pTsOH (150 mg) was added. After stirring for 30 min at room temperature, TLC indicated that the diethyl acetal had been converted to aldehyde. The reaction was quenched by the addition of anhydrous $K_2CO_3$ (500 mg). After removal of the solids by filtration, the filtrate was concentrated in vacuo to a dark oil that was chromatographed ($SiO_2$, hexanes/EtOAc) to provide 1.70 g (33%) of 6-methoxy-3-(4-formylbenzoyl-2-(4-methoxyphenyl)benzo[b]thiophene as a yellow solid. mp 147–150° C. $^1$H NMR (DMSO-d$_6$) δ10.03 (s, 1H), 7.85 (s, 4H), 7.70 (d, J=2.2 Hz, 1H), 7.57 (d, J=9.0 Hz, 1H), 7.28 (d, J=9.0 Hz, 2H), 7.06 (dd, J=9.0, 2.2 Hz, 1H), 6.84 (d, J=9.0 Hz, 2H), 3.67 (s, 3H), 3.86 (s, 3H). FD mass spec: 402.

EXAMPLE 1

(E)-6-methoxy-3-[4-(2-(carboxyvinyl)benzoyl]-2-(4-methoxyphenyl)]benzo[b]thiophene, ethyl ester

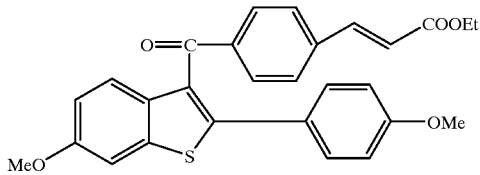

To a −78° C. solution of triethyl phosphonoacetate (0.70 mL, 3.43 mmol) in 20 mL of anhydrous THF under N$_2$ was added nBuLi (2.41 mL, 3.43 mmol, 1.6 M solution in hexanes) dropwise via syringe. After stirring for 20 min at −78° C. the solution was transferred via cannula to a −78° C. solution of 6-methoxy-3-(4-formylbenzoyl)-2-(4-methoxyphenyl)benzo[b]thiophene (1.15 g, 2.86 mmol) in 20 mL of anhydrous THF. The reaction mixture was allowed to gradually warm to room temperature whereupon the reaction was judged complete by TLC analysis. The reaction was quenched by distributing between H$_2$O/CHCl$_3$. The organic layer was dried (Na$_2$SO$_4$) and concentrated in vacuo to an oil that was chromatographed (SiO$_2$, CH$_2$Cl$_2$) to provide 1.25 g (93%) of (E)-6-methoxy-3-[4-(2-(carboxyvinyl)benzoyl]-2-(4-methoxyphenyl)benzo[b]thiophene, ethyl ester, as a yellow oil. $^1$H NMR (DMSO-d$_6$) δ7.74–7.66 (m, 5H), 7.62 (d, J=16.0 Hz, 1H), 7.45 (d, J=9.0 Hz, 1H), 7.30 (d, J=9.0 Hz, 2H), 7.03 (dd, J=9.0, 2.2 Hz, 1H), 6.87 (d, J=9.0 Hz, 2H), 6.70 (d, J=16 Hz, 1H), 4.19 (q, J=7.0 Hz, 2H), 3.85 (s, 3H), 3.69 (s, 3H), 1.25 (t, J=7.0 Hz, 3H). FD mass spec: 473. Anal. Calcd. for C$_{28}$H$_{24}$O$_5$So1.5 H$_2$0: C, 67.32; H, 5.45. Found: C, 67.09; H, 5.05.

EXAMPLE 2

(E)-6-methoxy-3-[4-(2-carboxyvinyl)benzoyl]-2-(4-methoxyphenyl)]benzo[b]thiophene

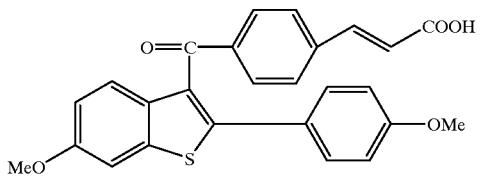

(E)-6-methoxy-3-[4-(2-(carboxyvinyl)benzoyl]-2-(4-methoxyphenyl)benzo[b]thiophene (1.15 g, 2.43 mmol) was dissolved with gentle warming on a steam bath in a mixture of 10 mL THF, 15 mL 2.0 N NaOH, and 5 mL of EtOH. After stirring for 1 h, the solution was acidified to pH 3 using 1.0 N HCl. The aqueous was extracted with EtOAc (3x). The organic was dried (Na$_2$SO$_4$) and concentrated to give 900 mg (83%) of (E)-6-methoxy-3-[4-(2-carboxyvinyl)benzoyl]-2-(4-methoxyphenyl)benzo[b]thiophene, as a yellow solid. mp 204–207° C. $^1$H NMR (DMSO-d$_6$) δ12.60 (bs, 1H), 7.69 (bs, 5H), 7.55 (d, J=16.0 Hz, 1H), 7.45 (d, J=9.0 Hz, 1H), 7.30 (d, J=8.5 Hz, 2H), 7.03 (dd, J=9.0, 2.2 Hz, 1H), 6.87 (d, J=8.5 Hz, 2H), 6.59 (d, J=16.0 Hz, 1H), 3.85 (s, 3H), 3.70 (s, 3H). FD mass spec: 444. Anal. Calcd. for C$_{26}$H$_{20}$O$_5$S: C, 70.26; H, 4.54. Found: C, 70.02; H, 4.55.

EXAMPLE 3

(E)-6-hydroxy-3-[4-(2-carboxyvinyl)benzoyl]-2-(4-hydroxyphenyl)benzo[b]thiophene

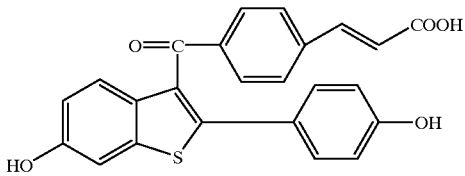

To a −5° C. solution of 6-methoxy-3-[4-(2-carboxyvinyl)benzoyl]-2-(4-methoxyphenyl)benzo[b]thiophene (900 mg, 2.0 mmol) in 40 mL of anhydrous CH$_2$Cl$_2$ under N$_2$ was added BBr$_3$ (0.76 mL, 8.0 mmol) slowly via syringe. After warming to 5° C., the mixture was stirred for 1 h at 5° C., then quenched by pouring into ice water (100 mL). The mixture was extracted with EtOAc (3×100 mL). The organic was then dried (Na$_2$SO$_4$) and concentrated in vacuo to a solid residue that was chromatographed (SiO$_2$, 1% MeOH/CHCl$_3$) to provide 730 mg (86%) of (E)-6-hydroxy-3-[4-(2-carboxyvinyl)benzoyl]-2-(4-hydroxyphenyl)benzo[b]thiophene as a yellow solid. mp 155–160° C. $^1$H NMR (DMSO-d$_6$) δ12.55 (bs, 1H), 9.81 (s, 1H), 9.73 (s, 1H), 7.67 (s, 4H), 7.54 (d, J=16.0 Hz, 1H), 7.40 (d, J=9.0 Hz, 1H), 7.30 (d, J=2.5 Hz, 1H), 7.18 (d, J=9.0 Hz, 2H), 6.89 (dd, J=9.0, 2.5 Hz, 1H), 6.65 (d, J=9.0 Hz, 2H), 6.58 (d, J=16.0 Hz, 1H). FD mass spec: 416. Anal. Calcd. for C$_{24}$H$_{16}$O$_5$S: C, 69.22; H, 3.87. Found: C, 68.95; H, 3.73.

EXAMPLE 4

6-hydroxy-3-[4-(2-carboxyethyl)benzoyl]-2-(4-hydroxyphenyl)benzo[b]thiophene

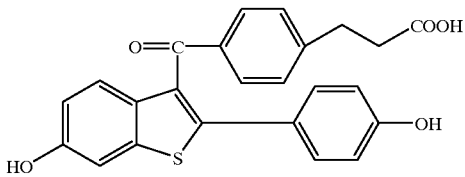

6-hydroxy-3-[4-(2-carboxyvinyl)benzoyl]-2-(4-hydroxyphenyl)benzo[b]thiophene (310 mg, 0.74 mmol) was dissolved in 50 mL of a 1:1 mixture of EtOH and EtOAc. This solution was hydrogenated at 40 psi in the presence of 10% Pd/C (200 mg). When the reaction was judged complete by TLC analysis, the mixture was filtered through Celite to remove the catalyst. The filtrated was concentrated in vacuo to a yellow oil that was triturated from hexanes/EtOAc. Filtration provided 225 mg (72%) of 6-hydroxy-3-[4-(2-carboxyethyl)benzoyl]-2-(4-hydroxyphenyl)benzo[b]thiophene as a yellow solid. mp 244–248° C. $^1$H NMR (DMSO-d$_6$) δ12.15 (bs, 1H), 9.74 (s, 1H), 9.68 (s, 1H), 7.56 (d, J=8.1 Hz, 2H), 7.30 (d, J=2.0 Hz, 1H), 7.23–7.19 (m, 3H), 7.12 (d, J=8.5 Hz, 2H), 6.82 (dd, J=9.0, 2.0 Hz, 1H), 6.62 (d, J=8.5 Hz, 2H), 2.77 (t, J=7.0 Hz, 2H), 2.45 (t, J=7.0 Hz, 2). FD mass spec: 418. Anal. Calcd. for C$_{24}$H$_{18}$O$_5$S.20 H$_2$0: C, 68.89; H, 4.34. Found: C, 68.35; H, 4.72.

Test Procedure

General Preparation Procedure

In the examples illustrating the methods, a post-menopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved or suspended in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay

Uteri were kept at 4° C. until time of enzymatic analysis. The uteri were then homogenized in 50 volumes of 50 mM Tris buffer (pH–8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound

17α-ethynyl estradiol was obtained from Sigma Chemical Co., St. Louis, Mo.

Influence of Formula I Compounds on Serum Cholesterol and Determination of Agonist Activity Data presented in Tables 1 and 2 below show comparative results among ovariectomized rats, rats treated with 17α-ethynyl estradiol ($EE_2$; an orally available form of estrogen), and rats treated with certain compounds of the present invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

The compounds of the present invention at a dose of 10 mg./kg. reduced serum cholesterol compared to the ovariectomized control animals. Uterine weight was somewhat increased but this increase was significantly less than was observed with $EE_2$.

As is expressed in the below data, estrogenicity also was assessed by evaluating the adverse response of eosinophil infiltration into the uterus. The compounds of the present invention did not cause any significant increase in the number of eosinophils observed in the stromal layer of ovariectomized rats, while estradiol cause a substantial, expected increase in eosinophil infiltration.

The data presented in Tables 1 and 2 below reflect the response of 5 to 6 rats per treatment.

TABLE 1

| Compound | Dose mg/kg | Uterine Weight (% increase vs. OVX) | Uterine EPO (V. max) | Serum Cholesterol (% decrease vs. OVX |
|---|---|---|---|---|
| $EE_2$ | 0.1 | 201.3 | 130.5 | 68.6 |
| Example 2 | 0.1 | 25.0 | 2.1 | −16.6 |
| CDX susp. | 1 | 23.3 | 2.1 | −37.3 |
|  | 10 | 119.9 | 35.1 | 73.2 |
| Example 3 | 0.1 | 23.9 | 0.9 | −15.1 |
| CDX soln. | 1 | 19.7 | 1.2 | −26.6 |
|  | 10 | 97.3 | 8.4 | 57.7 |
| Example 4 | 0.1 | −45.9 | 0.0 | −46.2 |
| CDX soln. | 1 | −37.0 | 0.0 | −28.8 |
|  | 10 | 29.3 | 1.2 | 16.5 |

TABLE 2

| Compound | Dose mg/kg | Uterine Weight (% increase vs. OVX) | Uterine EPO (V. max) | Serum Cholesterol (% decrease vs. OVX |
|---|---|---|---|---|
| EE2 | 0.1 | 197.3 | 216.3 | 93.8 |
| Example 3 | 0.1 | 3.1 | 0.9 | 20.7 |
| CDX soln. | 1 | 6.7 | 2.1 | 30.0 |
|  | 10 | 139.7 | 22.2 | 74.1 |

In addition to the demonstrated benefits of the compounds of the present invention, especially when compared to estradiol, the above data clearly demonstrate that compounds of Formula I are not estrogen mimetics. Furthermore, no deleterious toxicological effects (survival) were observed with any treatment.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin.

As used herein, the term "estrogen" includes steroidal compounds having estrogenic activity such as, for example, 17β-estradiol, estrone, conjugated estrogen (Premarin®), equine estrogen, 17β-ethynyl estradiol, and the like. As used herein, the term "progestin" includes compounds having progestational activity such as, for example, progesterone, norethylnodrel, nongestrel, megestrol acetate, norethindrone, and the like.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be preferred. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of Formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

The following formulation examples are illustrative only and are not intended to limit the scope of the present invention.

Formulations

In the formulations which follow, "active ingredient" means a compound of Formula I, or a salt or solvate thereof.

Formulation 1: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
|---|---|
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
|---|---|
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

| Formulation 4: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient | 50 mg |
| Isotonic saline | 1,000 mL |

The solution of the above ingredients is intravenously administered to a patient at a rate of about 1 mL per minute.

| Formulation 8: Combination Capsule I | |
|---|---|
| Ingredient | Quantity (mg/capsule) |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

| Formulation 9: Combination Capsule II | |
|---|---|
| Ingredient | Quantity (mg/capsule) |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

| Formulation 10: Combination Tablet | |
|---|---|
| Ingredient | Quantity (mg/capsule) |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:
1. A compound of the formula

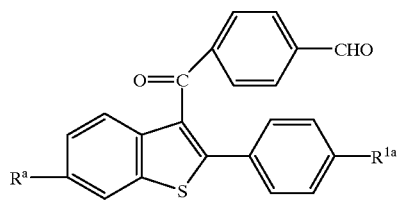

wherein each of $R^a$ and $R^{1a}$ is independently hydrogen, $C_1$–$C_4$-alkoxy, benzyloxy, $C_1$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_{1-5}$ alkoxycarbonyloxy, or $C_4$–$C_6$-alkylsulfonyloxy.

2. A compound of claim 1 wherein both of $R^a$ and $R^{1a}$ represent methoxy.

3. A method for the preparation of a compound of Formula Ib:

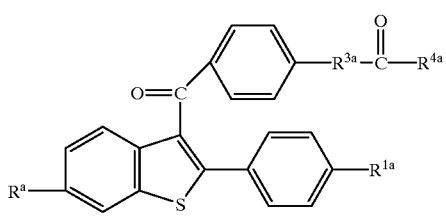

Ib wherein each of $R^a$ and $R^{1a}$ is independently hydrogen, $C_1$–$C_4$-alkoxy, benzyloxy, $C_2$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_{1-5}$-alkoxycarbonyloxy, or $C_4$–$C_6$-alkylsulfonyloxy;

$R^{3a}$ is —CH=CH—(trans); and $R^{4a}$ is $C_1$–$C_4$-alkoxy, which comprises reacting a compound of Formula Ia

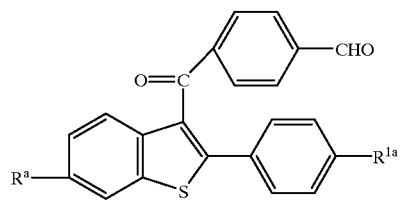

Ia with a trialkyl phosphonoacetate carbanion in an inert solvent at a temperature from −78° C. to 0°.

4. The process of claim 3 wherein both of $R^a$ and $R^{1a}$ are methoxy.

5. The process of claim 4 followed by hydrolysis and hydroxyl deprotection to the compound (E)-6-hydroxy-3-(4-(2-carboxyvinyl)benzoyl)-2-(4-hydroxyphenyl)benzo(b)thiophene.

6. The process of claim 5 followed by the further step of hydrogenation to the compound 6-hydroxy-3-(4-(2-carboxyethyl)benzoyl)-2-(4-hydroxyphenyl)benzo(b)thiophene.

* * * * *